United States Patent
Babes-Dornea et al.

(10) Patent No.: US 6,506,296 B2
(45) Date of Patent: Jan. 14, 2003

(54) MICRO-FUEL CELL SENSOR APPARATUS AND METHOD FOR MODELING THE SENSOR RESPONSE TIME

(75) Inventors: Elena Babes-Dornea, Pierrefonds (CA); Claude Beauchemin, Valleyfield (CA); Renyan Qin, Pierrefonds (CA)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/801,043

(22) Filed: Mar. 8, 2001

(65) Prior Publication Data

US 2002/0125131 A1 Sep. 12, 2002

(51) Int. Cl.$^7$ ............................................. G01N 27/404
(52) U.S. Cl. ...................... 205/775; 204/415; 204/432
(58) Field of Search ................................ 204/415, 431, 204/432; 205/775, 782.5, 783

(56) References Cited

U.S. PATENT DOCUMENTS

| | | | |
|---|---|---|---|
| 3,852,169 A | * | 12/1974 | Kring et al. |
| 3,966,579 A | * | 6/1976 | Chang et al. |
| 4,051,006 A | * | 9/1977 | Neti et al. |
| 4,271,474 A | | 6/1981 | Belanger et al. |
| 4,293,399 A | | 10/1981 | Belanger et al. |
| 5,200,044 A | * | 4/1993 | Milstein et al. |
| 5,667,653 A | * | 9/1997 | Schneider et al. |

* cited by examiner

*Primary Examiner*—T. Tung
(74) *Attorney, Agent, or Firm*—Nixon & Vanderhye

(57) ABSTRACT

An apparatus for measuring hydrogen content and partial hydrogen pressure in gas streams and a method of modeling the sensor based on the characteristics of the sensor. The apparatus includes a housing with micro-fuel cell sensor disposed therein. The sensor includes a sensing element having first and second gas diffusing electrodes spaced from one another with an acidic electrolyte disposed between the electrodes. A first gas permeable membrane separates the first electrode from an external gas stream. A second gas permeable membrane separates the second electrode from atmospheric air. Electrochemical charging of the first electrode occurs when hydrogen from a gas stream diffuses through the first membrane to react with the first electrode, while the potential of the second electrode remains unchanged. The potential difference between the first and second electrodes measured as current is identified to represent the sensor output. The response time of the sensor is modeled based on the characteristics of the sensor affecting the sensor response time.

14 Claims, 5 Drawing Sheets

| Sensor Identification | $T_{exp}$ sec | $R_{ext}$ ohm | V cm$^3$ | L cm | A cm$^2$ | $T_{calc}$ sec |
|---|---|---|---|---|---|---|
| Hydran | 100 | 500 | 1.2 | 5.00E-03 | 5 | 103 |
| Prototype2 | 7 | 50 | 0.01 | 5.00E-03 | 2.27 | 6.4 |
| Protytype2 (RATIO) Hydran | 0.07 | 0.1 | 0.008 | 1 | 0.45 | 0.06 |

MICRO-FUEL CELL SENSOR APPARATUS AND METHOD FOR MODELING THE SENSOR RESPONSE TIME

FIELD OF THE INVENTION

This invention relates to a sensor for the measurement of hydrogen content in gas streams. More particularly, it relates to a method for modeling the response time of the sensor.

BACKGROUND OF THE INVENTION

Industrial uses of hydrogen require a simple and sensitive device for detecting hydrogen leaks and for measuring hydrogen concentrations. Prior art detectors have a long response time to hydrogen. For example, one such detector sold under the trade name Hydran is devoted primarily for the continuous monitoring of slowly variable hydrogen concentrations and has a response time on the order of minutes. Several attempts have been made in the past to improve the response time of hydrogen detectors without much success.

Moreover, known hydrogen detectors failed to consider characteristics influencing the sensor response time. Thus, there is a need for an efficient sensor with a fast response time for analyzing hydrogen content and determining hydrogen partial pressure in gas streams.

BRIEF SUMMARY OF THE INVENTION

Accordingly, the present invention is directed to a micro-fuel cell sensor apparatus and method for the measurement of hydrogen content and hydrogen partial pressure in a gas stream. The sensor is disposed in a fuel-cell housing. The sensor includes a sensing element having first and second gas diffusing electrodes spaced from one another. A fuel-cell spacer having an acidic electrolyte is disposed between the two electrodes. The first electrode is spaced from a first gas permeable membrane by a first cavity, the first membrane being disposed proximate to the housing base.

A second gas permeable membrane is disposed opposite to the first membrane and away from the housing base. Oxygen from atmospheric air is continuously supplied to the second gas diffusing electrode by way of natural diffusion through the second gas permeable membrane. The second electrode is spaced from the second membrane by a second cavity. The amount of oxygen supplied to the second electrode exceeds the amount required for stochiometric reaction with hydrogen diffused through the first membrane.

The above described sensor is disposed in a sensor body having a chamber defined therein for accommodating the sensor. An external gas stream is received in the sensor body via an opening therein. A sensor cover having a recess sealingly mates with the sensor body, the recess in the cover opening into the chamber in the sensor body.

The sensor cover further includes a connector for providing electrical connection to the sensor and also for facilitating measurement of the sensor output. The sensor cover also includes a third gas permeable membrane for supplying oxygen by way of natural diffusion from atmospheric air. Oxygen diffused into the sensor body through the third membrane enters the sensor by way of further diffusion through the second membrane. Excess oxygen may be furnished at the second electrode by an appropriate selection of second and third membranes. The first membrane is chosen to have a high permeability to hydrogen and lower permeability to gases having molecular dimensions that are higher than hydrogen.

In its assembled state, when hydrogen from a gas stream diffuses selectively through the first membrane into the first cavity facing the first gas diffusing electrode, electrochemical charging of the first electrode occurs at a potential corresponding to hydrogen concentration in the first cavity, while the potential of the second electrode remains unchanged. The potential difference created between the first and second electrodes produces a current flow measured by connecting the first and second electrodes through a load resistance. The current measured as a voltage drop across the load resistance represents the micro-fuel cell sensor output.

In one aspect, the present invention thus provides a sensor for measuring partial hydrogen pressure in a gas stream, the sensor including a housing, a sensing element comprising first and second gas diffusing electrodes spaced from one another, a fuel-cell spacer having an acidic electrolyte disposed between the first and second electrodes, a first gas permeable membrane of thickness L and an active surface area A, separating the first electrode from the gas stream by a cavity of volume V, a second gas permeable membrane separating the second electrode from atmospheric air, and a load resistance R connecting the first and second electrodes, wherein a response time T of the sensor is determined by $T = aR + b(VL)/A$; where "a" and "b" are constants. Preferably, the first membrane has higher permeability to hydrogen and lower permeability to gases with molecular dimensions greater than that of hydrogen. The oxygen rate of permeation through the second membrane is higher than hydrogen rate of permeation through the first membrane, whereby oxygen furnished at the second electrode exceeds stochiometric oxygen necessary for the reaction with hydrogen. The first and second electrodes are preferably connected through a load resistance to measure the sensor output.

Oxygen furnished at the second electrode is controlled by an appropriate choice of the second membrane. The first and second membranes are preferably made of a polymeric material. A hydrogen partial pressure gradient is maintained between the first electrode and an external gas stream. The first and second electrodes are preferably identical.

In another aspect, the present invention provides an apparatus for measuring partial hydrogen pressure in a gas stream. The apparatus includes a housing, a micro-fuel cell sensor disposed in the housing, a cover member, the sensor including a sensing element having first and second gas diffusing electrodes spaced from one another, a fuel-cell spacer with an acidic electrolyte interposed between the first and second electrodes, a first gas permeable membrane, of thickness L and an active surface area A, spaced from the first electrode by a cavity of volume V, a second gas permeable membrane spaced from the second electrode to supply oxygen to the second electrode by natural diffusion of atmospheric air, and a load resistance R connecting the first and second electrodes, wherein response time T of the sensor is determined by $T = aR + b(VL)/A$; where "a" and "b" are constants. The cover member includes a connector for providing an electrical connection to the sensor, a third gas permeable membrane disposed in one of the cover member and the housing for receiving atmospheric air. The apparatus further includes means for sealingly attaching the housing to an assembly carrying a gas stream.

In yet another aspect, the present invention provides a method for determining the response time of the micro-fuel cell sensor according to the equation $T = (a.R + b.(V.L)/A)$; where "a" and "b" are constants.

BRIEF DESCRIPTION OF THE DRAWINGS

FIG. 5 shows a table illustrating the experimental and calculated response times of various hydrogen sensors including the micro-fuel sensor of the present invention identified as Prototype 2.

DETAILED DESCRIPTION OF THE INVENTION

Figure 1:
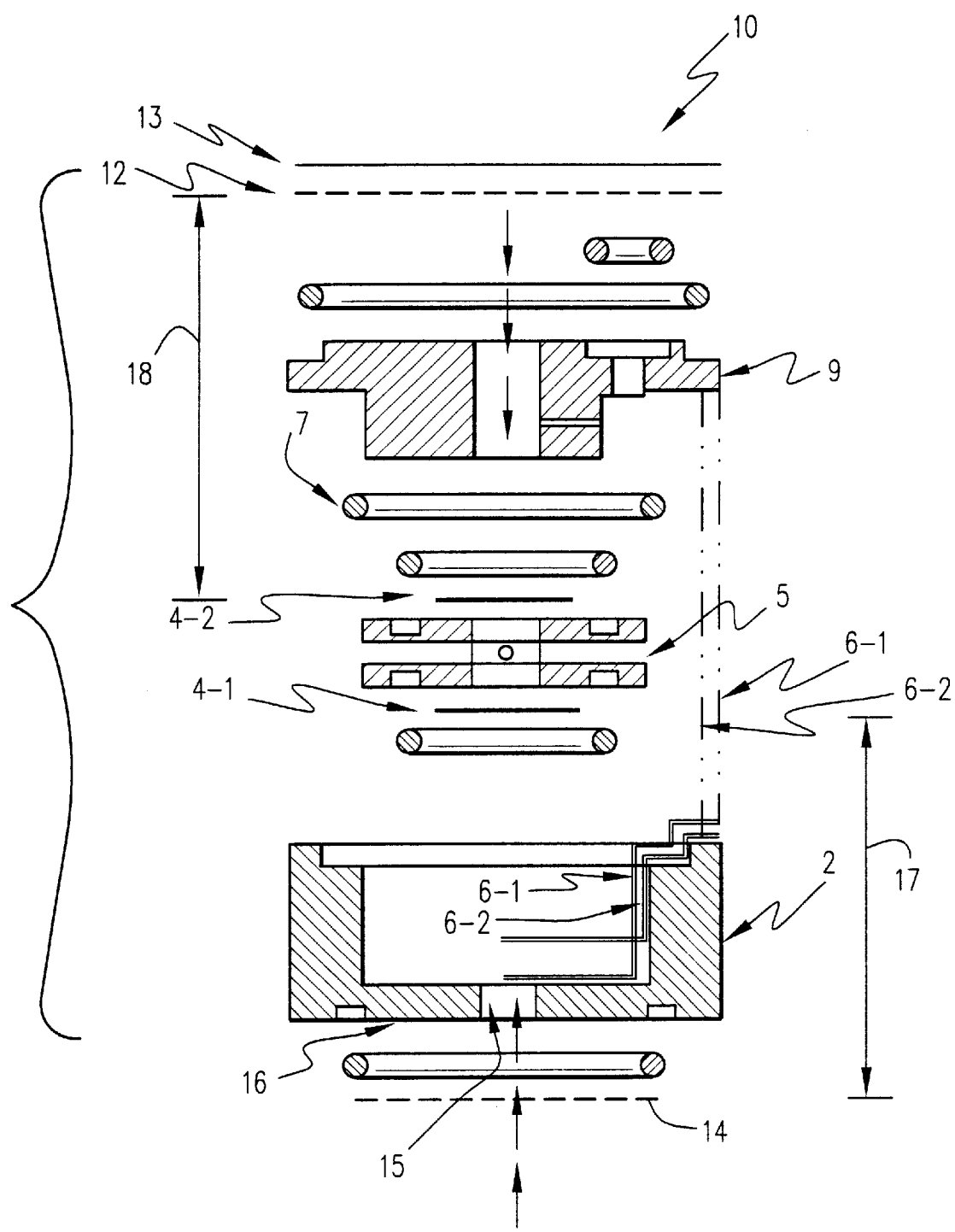
FIG. 1 is an exploded cross-sectional view of a micro-fuel cell sensor assembly.
Figure 3:
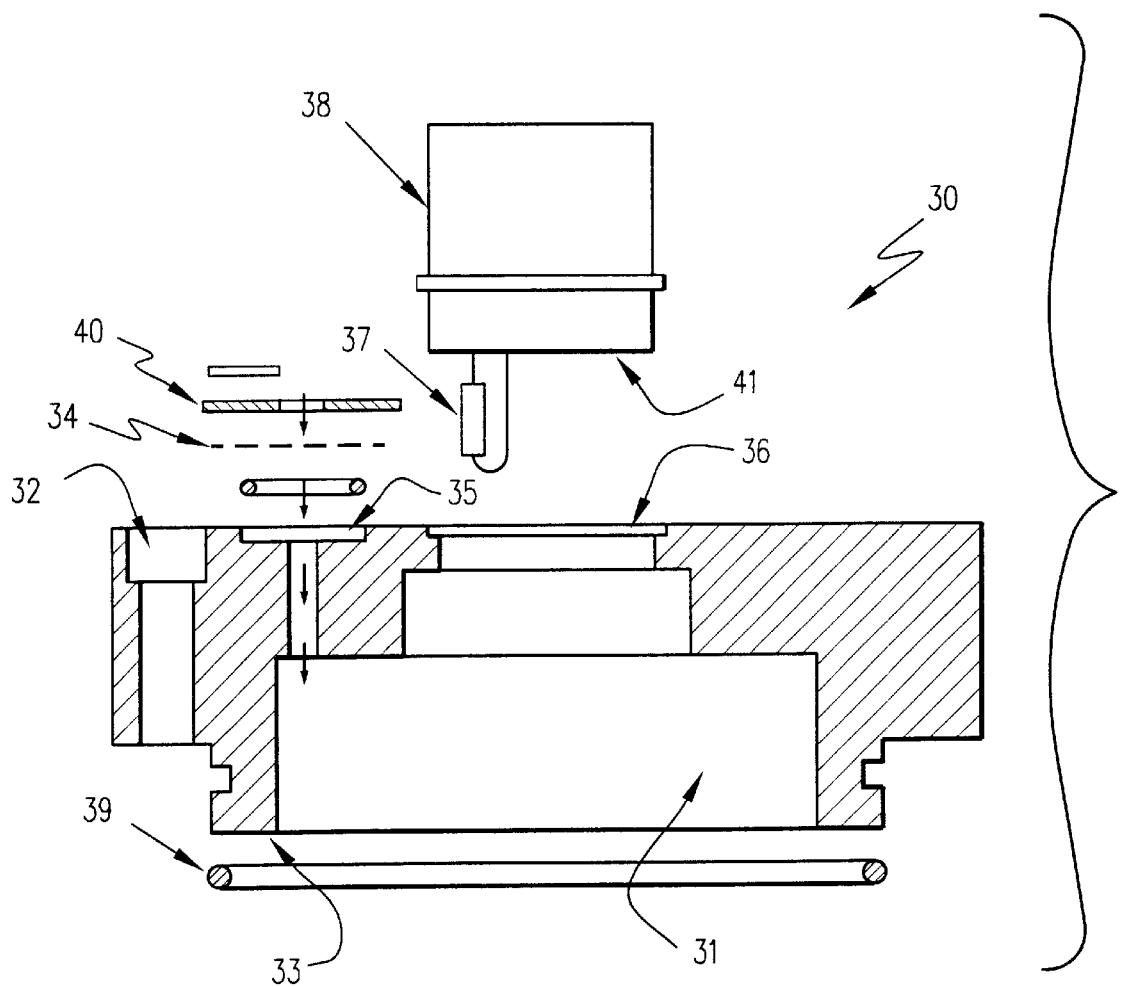
FIG. 3 is a cross-sectional view of a cover assembly of the micro-fuel cell sensor body of FIG. 2.

In FIG. 1 there is illustrated a detailed view of a micro-fuel cell sensor assembly 10 for measuring partial hydrogen pressure in gas streams. The sensor 10 includes a fuel-cell housing 2 having a base portion 16 and a fuel-cell cover 9. An aperture 15 is defined in the base portion 16 for facilitating diffusion of hydrogen from an external gas stream into a first cavity 17. The sensing element of the sensor 10 includes a first electrode 4-1 disposed in housing 10 towards the base portion 16. A second electrode 4-2 is disposed opposite to the first electrode 4-1 with a fuel-cell spacer 5 comprising an acidic electrolyte disposed therebetween. A first membrane 14 is disposed on base portion 16 to separate the first electrode 4-1 from an external gas stream. The first membrane 14 is spaced from the first electrode 4-1 by a first cavity 17. A second membrane 12 is disposed adjacent to the fuel cell cover 9 and separates the second electrode 4-2 from atmospheric air diffusing into the sensor body through a third gas permeable membrane 34 as illustrated in FIG. 3. The second membrane 12 is spaced from the second electrode 4-2 by a second cavity 18. The second cavity 18 is continuously supplied with oxygen by natural diffusion from the atmospheric air through the second membrane 12. Excess oxygen may be furnished at the second electrode 4-2 by an appropriate choice of the second membrane 12. The second membrane 12 is chosen to supply the second electrode 4-2 with an excess amount of oxygen than otherwise required for a stochiometric reaction with diffused hydrogen. The concentration polarization of the second electrode 4-2 may thus be avoided, realizing a sensor with anodic control. Sensor leads 6-1 and 6-2 are disposed in housing 2 to contact first and second electrodes 4-1 and 4-2, respectively. Output of the sensor 10 is measured between the sensor leads 6-1 and 6-2 through a resistor 37 as illustrated in FIG. 3.

Figure 2:
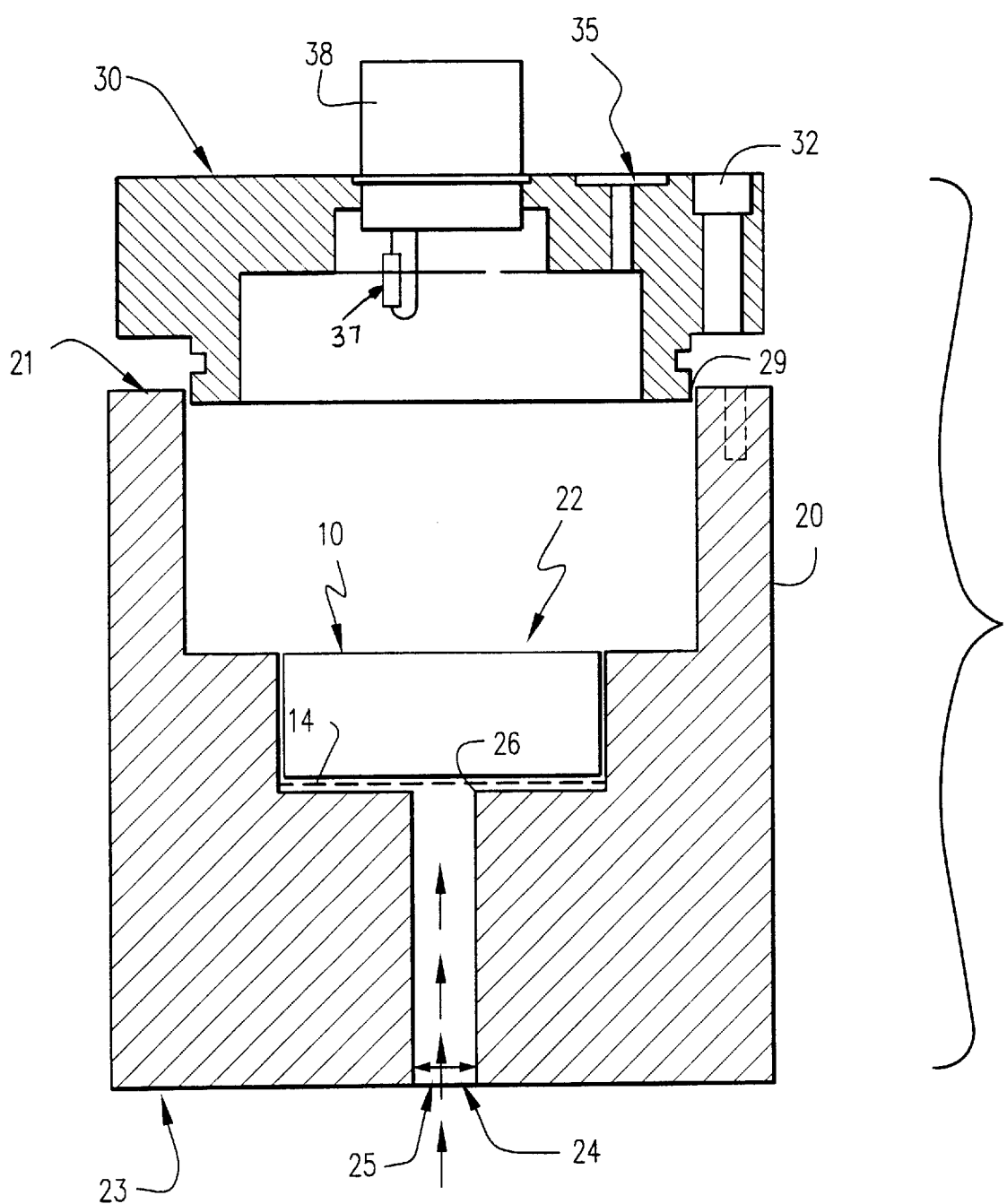
FIG. 2 is a cross-sectional view a micro-fuel cell sensor body, with cover assembly as shown in FIG. 3, for accommodating the micro-fuel cell sensor of FIG. 1.

The sensor 10 as described above is adapted to be placed in a sensor body 20 as illustrated in FIG. 2. The sensor body 20 includes an upper portion 21 and a lower base portion 23 with an aperture 24 defined therein. An external gas stream is received in the sensor body 20 through orifice 25 defined between apertures 24, 26. An opening 22 in sensor body 20 accommodates sensor 10. Aperture 15 communicates with aperture 26 defined in opening 22 of sensor body 20.

FIG. 3 illustrates a cover member 30 for covering the sensor body 20 in an airtight manner. Cover member 30 includes a slot 31 having an upper end 36 and a lower end 33. The cover member 30 sealingly covers the sensor body 20 as illustrated in FIG. 2. Cover member 30 further includes a vent 35 for permitting oxygen from atmospheric air to enter the second cavity 18 of sensor 10 through slot 31. At least one fastener may be used to secure the cover member 30 to the sensor body 20 as illustrated in FIG. 2. The third gas permeable membrane 34 separates vent 35 from the atmospheric air. A perforated vent cover plate 40 overlies and protects the third membrane. A connector member 38 having a end portion 41 is disposed in an airtight manner in the upper portion 36 of slot 31. The connector 38 includes a resistor 37 which projects out into the upper portion 36 of slot 31. Sensor leads 6-1 and 6-2 connected on one side to the first electrode 4-1 and 4-2, respectively, terminate in connector 38. The output of the sensor 10 is represented by the potential difference between sensor leads 6-1 and 6-2 through resistor 37.

In its assembled state, the base portion 23 of the sensor body 20 is adapted to be tightly attached on assemblies carrying a gas stream to measure hydrogen content in the gas stream. In this state, the upper portion 21 of the sensor body faces atmospheric air. Thus, the second cavity 18 facing the second electrode 4-2 is continuously supplied with oxygen by natural diffusion from the atmospheric air. Hydrogen gas present in the gas stream enters the sensor through aperture 24, diffuses through the first membrane 14 to enter the first cavity 17 in order to contact the first electrode 4-1. The first and second electrodes may have noble metal electro-catalyst and graphite paper or carbon cloth backing. Since the first membrane 14 is a chosen to have high permeability to hydrogen, but is less permeable to gases with higher molecular dimensions than hydrogen, the sensor is primed to be highly selective for hydrogen.

Selective diffusion of hydrogen gas from a gas stream through the first membrane 14 into the first cavity 17 causes electrochemical charging of the first electrode 4-1 at a potential corresponding to the hydrogen concentration in the first cavity 17 facing the first electrode 4-1, while the potential at the second electrode 4-2 remains unchanged. The potential difference created between the first and second electrodes produces a current flow by connecting the electrodes through a resistor 37. This current measured as a voltage drop across the resistor 37 represents the sensor output. In the illustrated configuration of the sensor, the first membrane 14 is a diffusion barrier for the linearity of the sensor output toward hydrogen concentration. Since the hydrogen concentration at the first electrode 4-1 is always zero, and since the sensor 10 consumes the hydrogen at a faster rate than the rate of permeation through the first membrane, as long as hydrogen is present in the gas stream, a partial pressure gradient between the outside and the inside of the sensor exists, thus permitting diffusion of hydrogen into the sensor.

Figure 4:
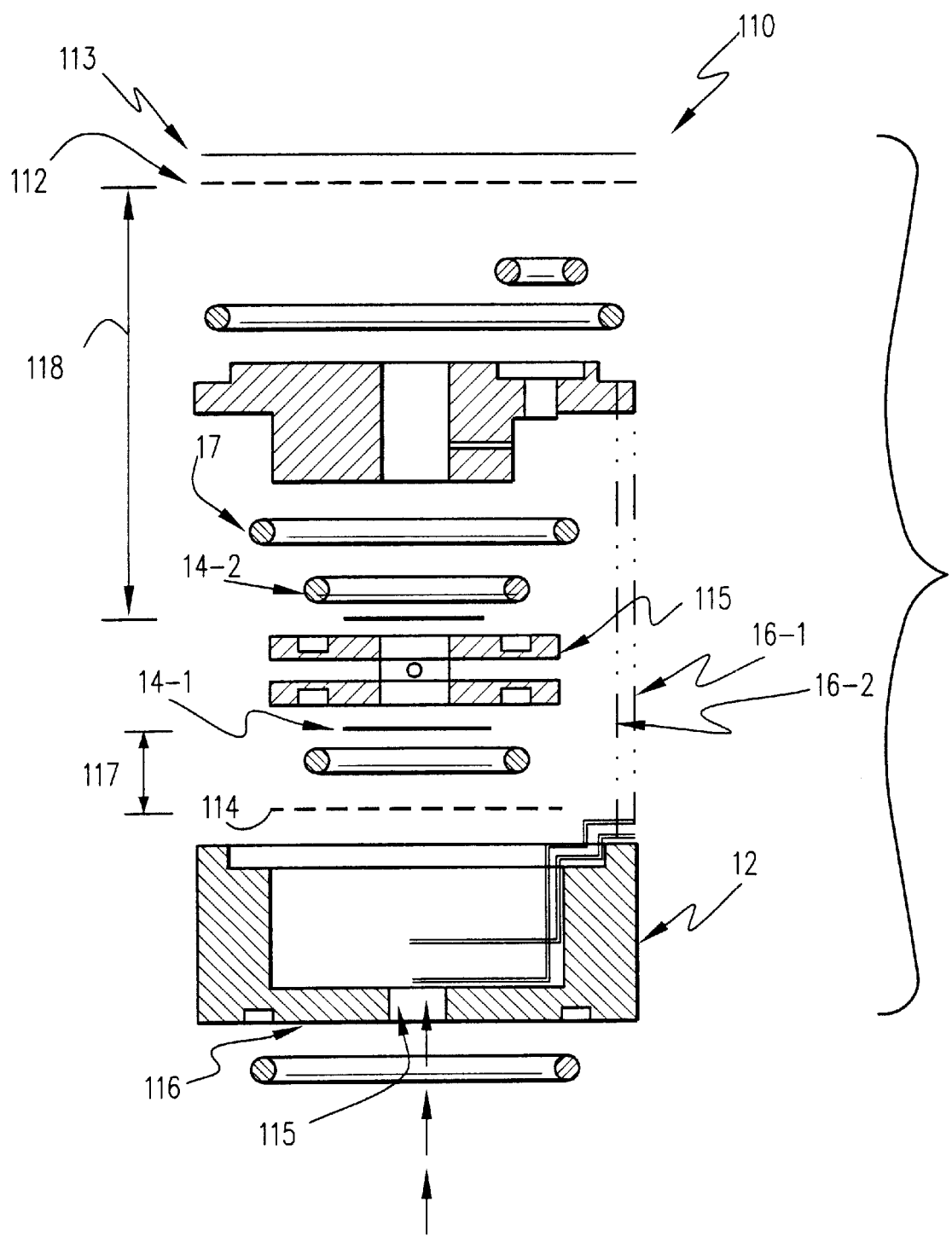
FIG. 4 is a cross-sectional view of another embodiment of the invention wherein the first gas permeable membrane is located adjacent to the first gas diffusing electrode.

Referring now to FIG. 4, a second embodiment is illustrated where elements in common with the sensor of FIG. 1 are indicated by similar reference numerals, but with a prefix "1" added. Here, the first membrane 114 is located on or directly adjacent the surface of the first electrode 14-1 to reduce the response time of sensor 110. Typically, a sensor with a fast response time is desired for the analysis of hydrogen content in gas streams. By locating the first membrane 114 on the surface of the first electrode, the volume (V) of the first cavity 17 is modified, thus modifying the response time (T) of the sensor. Other characteristics that influence the sensor response time include, for instance, the nature of the electro-catalyst and the electrolyte, electrical parameter values for the elements used in the equivalent circuit of the sensor, internal resistance of the sensor, and external load resistance (R). Further, the rate of hydrogen permeability through the first membrane 114 is a function of the nature of the membrane material and its geometry, the membrane thickness (L) and its active surface area (A). The sensor response time (T) may be modeled by the following equation:

$$T=a.R+b.(VL)/A; \text{ where "}a\text{" and "}b\text{" are constants} \qquad (1)$$

The constants indicated in equation (1) may be established under given conditions of temperature surrounding the sensor, and hydrogen content in a gaseous stream. In an example embodiment, at a temperature of 60 degrees Centigrade with 10% hydrogen content in a nitrogen gas stream having a flow rate of 5 slpm, with the acidic electrolyte comprising of sulfuric acid, and the first membrane being made of Teflon, the constants "a" and "b" are approximated to be 0.11 and 40,000, respectively. The sensor response time (T), however, is independent of hydrogen concentration and flow rate of hydrogen. The sensor response time (T) may be approximated, using the values of the constants, as follows:

$$T=0.11R+4\times10^4(VL)/A \qquad (2)$$

Equation 2, as above, may be used to approximate the sensor response time (T) for the sensor parameters within the following ranges:

V: 0.01 to 1.2 cm$^3$; L: 10$^{-3}$ to 5×10$^{-3}$ cm; A: 0.2 to 5 cm$^2$

Referring now to FIG. 5, there is shown a Table I illustrating the experimental and calculated response times of various hydrogen sensors including the micro-fuel sensor of the present invention identified as Prototype 2 in Table I. As clearly evident from Table I, the response time of the present sensor is around 7 seconds as compared to the response time of prior art Hydran sensor which is around 100 seconds. Thus, the response time of the present sensor is significantly small when compared to prior art hydrogen sensors, thus providing a clear advantage in analyzing hydrogen content in gas streams.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A micro-fuel cell sensor for measuring partial hydrogen pressure in a gas stream, comprising:
    a housing;
    a sensing element comprising first and second gas diffusing electrodes spaced from one another, said sensing element disposed in said housing;
    a fuel-cell spacer having an acidic electrolyte disposed between said first and second electrodes;
    a first gas permeable membrane, of thickness (L) and an active surface area (A), separating said first electrode from the gas stream and enabling hydrogen diffusion therethrough, said first membrane being spaced from said first electrode by a first cavity of volume (V) enabling hydrogen diffused through said first membrane to contact said first electrode;
    a second gas permeable membrane separating said second electrode from atmospheric air and defining a second cavity therewith isolated from said first cavity;
    means for substantially precluding contact of hydrogen in said first cavity with said second electrode; and
    a load resistance (R) connecting said first and second electrodes, wherein a response time (T) of said sensor is determined by $$T=aR+b(VL)/A;$$

where "a" and "b" are constants.

2. The sensor of claim 1, wherein said first membrane has higher permeability to hydrogen and lower permeability to gases with molecular dimensions greater than that of hydrogen.

3. The sensor of claim 2, wherein oxygen rate of permeation through said second membrane is higher than hydrogen rate of permeation through said first membrane, whereby oxygen furnished at said second electrode exceeds stochiometric oxygen necessary for the reaction with hydrogen.

4. The sensor of claim 3, wherein oxygen furnished at said second electrode is controlled by an appropriate choice of said second membrane.

5. The sensor of claim 4, wherein said first and second membranes are made of a polymeric material.

6. The sensor of claim 4, wherein a hydrogen partial pressure gradient is maintained between said first electrode and an external gas stream.

7. The sensor of claim 3, wherein said first and second electrodes are identical.

8. A sensor according to claim 1 wherein said first membrane is located on a surface of the first electrode to provide a reduced first volume to increase the hydrogen concentration for a given first membrane.

9. An apparatus for measuring partial hydrogen pressure in a gas stream, comprising:
    a housing;
    a micro-fuel cell sensor disposed in said housing;
    a cover member;
    said sensor comprising:
        a sensing element comprising first and second gas diffusing electrodes spaced from one another;
        a fuel-cell spacer having an acidic electrolyte disposed between said first and second electrodes;
        a first gas permeable membrane, of thickness (L) and an active surface area (A), separating said first electrode from a gas stream entering the sensor, said first membrane spaced from said first electrode by a cavity of volume (V);
        a second gas permeable membrane separating said second electrode from atmospheric air;
        means for isolating the first cavity and the second electrode from one another to substantially preclude contact of hydrogen in said first cavity with said second electrode; and
        a load resistance (R) connecting said first and second electrodes, whereby the response time T of the sensor is determined by the equation $$T=aR+b(VL)/A;$$

where "a" and "b" are constants.

10. The sensor of claim 9, wherein said cover member further comprises:
    a connector for providing an electrical connection to said sensor; and
    a third gas permeable membrane disposed in one of said cover member and said housing for receiving atmospheric air.

11. The sensor of claim 10, further comprises:

means for sealingly attaching said housing to an assembly carrying a gas stream.

12. The sensor of claim 10, wherein the space between said second electrode and said second membrane is supplied with oxygen by natural diffusion from atmospheric air.

13. The sensor of claim 12, wherein said first membrane is selected to have higher permeability to hydrogen and lower permeability to gases with molecular dimensions greater than that of hydrogen.

14. In a sensor having a housing, a sensing element including first and second gas diffusing electrodes spaced from one another, first and second gas permeable membranes spaced from said first and second gas diffusing electrodes, respectively, said first membrane having a thickness (L) and an active surface area (A), a cavity of volume (V) separating said first electrode and said first membrane and in which cavity hydrogen is received, means for Isolating the second electrode and the hydrogen in the cavity from one another, a load resistance (R) connecting said first and second electrodes, a method for measuring partial hydrogen pressure in a gas stream comprising:

determining the response time (T) of the sensor according to the equation $$T = aR + b(V.L)/A;$$

where "a" and "b" are constants.

* * * * *